United States Patent
Clemensen et al.

(10) Patent No.: US 9,265,444 B2
(45) Date of Patent: Feb. 23, 2016

(54) COMBINATION OF INERT GAS REBREATHING AND MULTIPLE-BREATH WASH-OUT TECHNIQUES FOR DETERMINATION OF INDICES OF VENTILATION INHOMOGENEITY

(75) Inventors: Peter Christian Clemensen, Odense C (DK); Jorgen Gronlund Nielsen, Glamsbjerg (DK)

(73) Assignee: IPR Holding ApS, Glamsbjerg (DK)

( * ) Notice: Subject to any disclaimer, the term of this patent is extended or adjusted under 35 U.S.C. 154(b) by 250 days.

(21) Appl. No.: 12/904,543

(22) Filed: Oct. 14, 2010

(65) Prior Publication Data
US 2011/0098589 A1    Apr. 28, 2011

(30) Foreign Application Priority Data
Oct. 15, 2009   (EP) .................................. 09013044

(51) Int. Cl.
*A61B 5/08*   (2006.01)
*A61B 5/087*   (2006.01)
*A61B 5/093*   (2006.01)

(52) U.S. Cl.
CPC ............... *A61B 5/0813* (2013.01); *A61B 5/087* (2013.01); *A61B 5/093* (2013.01)

(58) Field of Classification Search
CPC .......... A61B 5/08; A61B 5/082; A61B 5/091; A61B 5/0813
USPC .................................................. 600/529–543
See application file for complete search history.

(56) References Cited

U.S. PATENT DOCUMENTS 4,307,730 A * 12/1981 Korn ............................. 600/541
5,590,651 A *  1/1997 Shaffer et al. ................. 600/532

(Continued)

FOREIGN PATENT DOCUMENTS

| EP | 1510232 | 3/2005 |
|----|---------|--------|
| EP | 1767235 | 3/2007 |

(Continued)

OTHER PUBLICATIONS

Horsley, Alex. "Lung Clearance Index in the Assessment of Airways Disease." Respiratory Medicine (2009) 103, 793-799. Available online Feb. 25, 2009.*
Wanger et al. "Standardisation of the Measurement of Lung Volumes." Eur Respir J 2005; 26: 511-522.*
Horsley et al. "Lung clearance index is a sensitive, repeatable and practical measure of airways disease in adults with cystic fibrosis." Thorax 2008; 63: 135-140. Published Online First Aug. 3, 2007.*

(Continued)

*Primary Examiner* — Patricia Mallari
*Assistant Examiner* — Meredith Weare
(74) *Attorney, Agent, or Firm* — Gearhart Law, LLC

(57) ABSTRACT

The present invention discloses a method to determine the lung clearance index (LCI) or other indices of ventilation inhomogeneity of the lungs by combining two pulmonary gas exchange techniques; Inert gas rebreathing (IGR) is used for rapid wash-in of the inert tracer gas and for accurate determination of the functional residual capacity (FRC) by gas analysis alone. This is followed by multiple-breath wash-out (MBW) for determination of the cumulative expired volume ($V_{CE}$) required to clear the inert tracer gas from the lungs, and calculation of the LCI as the ratio between $V_{CE}$ and FRC. The advantages of the method are i) significant reduction of required test time, ii) significant reduction of consumed gas mixture for wash-in of tracer gas, iii) potential for further reduction of the use of tracer gas, and iv) more accurate determination of the FRC by gas dilution alone. Furthermore the present invention relates to a corresponding system and computer-readable medium.

16 Claims, 5 Drawing Sheets

(56) References Cited

U.S. PATENT DOCUMENTS

| | | |
|---|---|---|
| 8,201,557 B2 * | 6/2012 | Nielsen et al. ............ 128/204.22 |
| 2007/0021681 A1 * | 1/2007 | Sokoloff ....................... 600/529 |
| 2007/0144520 A1 | 6/2007 | Heinonen |
| 2008/0161711 A1 * | 7/2008 | Orr et al. ....................... 600/532 |
| 2015/0202400 A1 * | 7/2015 | Clemensen ......... A61M 31/005 600/431 |

FOREIGN PATENT DOCUMENTS

| | | | |
|---|---|---|---|
| WO | 2008/014788 | 2/2008 | |
| WO | WO 2008014788 A2 * | 2/2008 | ............. A61B 5/029 |

OTHER PUBLICATIONS

Guldbrand, Anna. "A comparison of helium dilution and plethysmography in measuring static lung volumes." Uppsala Universitet. 2008. 54 pages.*

Jonmarker et al. "Measurement of Functional Residual Capacity by Sulfur Hexafluoride Washout." Anesthesiology. 63:89-95, 1985.*

Gustafsson et al. "Measurement of Functional Residual Capacity and Ventilation Inhomogeneity by Gas Dilution Techniques." Hammer et al. (eds.) Paediatric Pulmonary Function Testing. Prog Respir Res. Basel, Karger, 2005, vol. 33, pp. 54-65.*

* cited by examiner

COMBINATION OF INERT GAS REBREATHING AND MULTIPLE-BREATH WASH-OUT TECHNIQUES FOR DETERMINATION OF INDICES OF VENTILATION INHOMOGENEITY

FIELD OF THE INVENTION

The present invention relates to a combination of techniques to determine the lung clearance index (LCI) or other indices of ventilation inhomogeneity of the lungs. Inert gas rebreathing (IGR) is used for rapid wash-in of the inert tracer gas and for accurate determination of the functional residual capacity (FRC) by gas analysis alone. This is followed by multiple-breath wash-out (MBW) for determination of the cumulative expired volume ($V_{CE}$) required to clear the inert tracer gas from the lungs and calculation of the LCI as the ratio between $V_{CE}$ and FRC.

BACKGROUND

Spirometry, i.e. the measurement of inspired and expired air flows and volumes at the airway opening of a test subject, is the commonest means of assessing lung function. Diseases causing obstruction of larger airways will eventually result in reduced expiratory flows and volumes as measured by spirometry. However, spirometry findings are often normal in the early stages of peripheral airway diseases, and therefore changes (obstruction or restriction) in the peripheral airways associated with early cystic fibrosis disease, early chronic obstructive pulmonary disease or mild asthma cannot be detected by spirometry until the disease has progressed considerably because the small airways only contribute to a very limited extent to the total airway resistance.

Peripheral airway diseases do, however, affect the way air mixes within the lungs and thus lead to increased ventilation inhomogeneity. Ventilation inhomogeneity may be assessed using the multiple-breath wash-out (MBW) test performed by washing out either a resident gas (e.g. nitrogen) from the lungs using e.g. pure oxygen or a previously washed-in non-resident inert tracer gas during tidal breathing of room air.

When using the MBW method to assess ventilation distribution in the lungs, several indices of overall ventilation inhomogeneity can be calculated as sensitive tracers of airway disease. They all reflect differences in specific ventilation between large and/or relatively small lung regions, resulting in delayed wash-out of the tracer gas from the poorly ventilated regions. Examples of indices of overall ventilation inhomogeneity that can be calculated from the MBW are mixing ratio (MR), which is calculated as the ratio between the actual and the estimated ideal number of breaths needed to lower the end-tidal tracer gas concentration to a certain fraction of the starting value, moment ratios of the wash-out curve and lung clearance index (LCI). The LCI can be calculated as the cumulative expired volume ($V_{CE}$) required to clear the gas from the lungs minus the number of wash-out breaths multiplied by external dead space outside the lips, divided by the subject's FRC (up to the lips). FRC is the amount of air that stays in the lungs after a normal expiration. In other words, LCI represents the number of lung volume turnovers (i.e. FRCs) that the subject must breathe to clear the lungs from the tracer gas (by convention, to an end-tidal concentration of 1/40th of the starting concentration over three subsequent breaths). Disregarding the correction for external dead space the equation is:

$$LCI = \frac{V_{CE}}{FRC} \quad (1)$$

The LCI is simple to calculate and intuitively understandable, and it is questionable whether any other index is more sensitive, reliable and clinically useful.

For the MBW test using a non-resident inert tracer gas there are several different gases with low solubility in blood and tissues that can be used including helium (He) and sulfur hexafluoride ($SF_6$). Normally, a respiratory mass spectrometer is used for the gas analysis, and a flowmeter, e.g. a pneumotachometer, is used to record the inspiratory and expiratory flows at the mouth. The pressure gradient measured is directly related to flow thus allowing a computer to derive a flow-curve measured in L/minute. The test subject is breathing through a mouthpiece or a face mask connected to the flowmeter, and a gas sampling tube is connected to the breathing assembly for sidestream gas analysis. When performing MBW tests by use of a non-resident tracer gas, the tracer gas must first be washed in to obtain an even concentration in the lungs before the wash-out can start. A conventional breath-by-breath system for inert gas wash-out therefore further consists of a unit for delivering the wash-in gas mixture. This can be achieved by use of a bias flow of the gas mixture. A sufficiently long wash-in period is needed to allow the tracer gas to fully equilibrate in the lungs, which may take quite some time. Conventional wash-in by use of a bias flow also results in a significant consumption of gas because the bias flow must exceed the peak inspiratory flow of the test subject. Alternative setups, such as a demand valve, can be used but may lead to increased external dead space and resistance to breathing.

The wash-out phase is initiated by disconnecting the bias flow during expiration. The wash-out should continue until the end-tidal tracer gas concentration has fallen below 1/40th of the starting concentration over three successive breaths.

Guidelines on lung function testing recommend that the MBW test be repeated in order to obtain at least two tests in which the difference between two FRC values is less than 10% when comparing the higher to the lower FRC value.

In the conventional MBW test the FRC is calculated from the net volume of inert gas exhaled divided by the difference in end-tidal fractional concentration at the start and end of the wash-out:

$$FRC = \frac{\text{Net volume of inert gas exhaled}}{C_{ET,start} - C_{ET,end}} \quad (2)$$

As the net volume of inert gas exhaled (numerator) is obtained by integration of the product of respiratory flow and fractional tracer gas concentration (i.e. expired and re-inspired tracer gas volumes on a breath-by-breath basis), accurate determination of the FRC requires a rapid dynamic response and data acquisition rate of the gas analyser. Proper alignment in time of the respiratory flow signal and fractional tracer gas concentration prior to the calculation is also critical. This makes demands on the performance of the gas analyser and the calibration of the equipment.

OBJECT AND SUMMARY OF THE INVENTION

The object of the present invention is to provide a method to avoid the main problems in the determination of the lung clearance index.

This is accomplished by using a method to determine the lung clearance index (LCI) of a test subject, said method comprising the steps of:
rebreathing of an inert tracer gas to wash-in the inert tracer gas until a constant concentration of the inert tracer gas is reached;
multiple-breath wash-out until the end-tidal tracer gas concentration has fallen below a predetermined fraction of the starting concentration;
wherein
the lung clearance index (LCI) is determined in steps of:
determining the functional residual capacity (FRC) by gas analysis alone from the inert gas rebreathing;
determining the cumulative expired volume ($V_{CE}$) required to clear the inert tracer gas concentration from the lungs below a predetermined fraction of the starting concentration;
calculation of the LCI as the ratio between $V_{CE}$ and FRC.

The method combines two pulmonary gas exchange techniques; inert gas rebreathing (IGR) is used for rapid wash-in of an inert tracer gas and for accurate determination of the functional residual capacity (FRC) by gas analysis alone, and multiple-breath wash-out (MBW) is used for determination of the cumulative expired volume ($V_{CE}$) required to clear the inert tracer gas from the lungs.

The rebreathing method is a more effective manoeuvre to obtain good mixing of the gases compared to multiple-breath wash-in.

In one embodiment the method uses a gas mixture containing the inert tracer gas, $SF_6$.

In one embodiment the method uses an oxygen enriched gas mixture comprising the inert tracer gas to avoid oxygen deficiency during the rebreathing manoeuvre.

A volume of the gas mixture corresponding to the test subject's resting tidal volume is filled into a rebreathing bag. The test subject is connected to the bag via a valve. At the end of an expiration the valve is opened and the subject then inhales the gas mixture from the bag and rebreathes the gas mixture in the closed rebreathing assembly until the inert gas is well mixed in the lungs (see FIG. 3 for setup for wash-in/wash-out tests using inert gas rebreathing).

Computer simulations have shown that rebreathing results in 5-10 times faster equilibration of the inert gas than open-circuit multiple-breath wash-in, and since the traditional open-circuit wash-in phase lasts longer than the subsequent wash-out phase, this means a reduction of total test time by typically more than 50%. See e.g. FIG. 4 which shows a comparison of inert gas rebreathing (used as part of the invention) and open-circuit multiple-breath wash-in (prior art) using data from computer simulations.

Use of rebreathing also reduces the total volume of gas mixture used. By rebreathing the volume is equal to the resting tidal volume ($V_T$) of the test subject, e.g. 0.6 liters in an adult. By multiple-breath wash-in the volume exceeds the peak inspiratory flow times the total wash-in time since the by-pass flow must exceed the peak inspiratory flow. As an example, assuming that the peak inspiratory flow equals three times the tidal volume per each half breath cycle, the by-pass flow must exceed V' peak=$6 \times V_T \times f_B$, where $f_B$ is the respiratory rate (breaths/minute). For a total wash-in time of e.g. 2 minutes by open-circuit wash-in the consumption of gas mixture would be 12 min$\times V_T \times f_B$, or, for a breathing frequency of e.g. 15 breaths per minute this would equal 180$\times V_T$. Thus, the gas consumption by rebreathing would be at least 180 times less than in the case of open-circuit wash-in. In case the gas mixture was inspired from a large non-diffusing bag in the open-circuit mode, the gas usage by rebreathing would be lower by a factor corresponding to the number of open-circuit wash-in breaths, i.e. the total wash-in time times the breathing frequency. Again, for a 2 minute open-circuit wash-in period, and a breathing frequency of 15 breaths per minute, the gas consumption would be 30 times less than in the open-circuit mode.

Combining the inert gas rebreathing technique with the use of a sensitive gas analyser (i.e. one with a high signal-to-noise ratio), for example based on photoacoustic spectroscopy (PAS) instead of a mass spectrometer as most frequently used in the known art, the consumption of gas would be minimized drastically. In one embodiment the inert gas rebreathing technique is combined with a sensitive $SF_6$ analyser whereby the consumption of $SF_6$ would be minimized drastically. A PAS analyser exists which has a unique sensitivity to $SF_6$ and is able to measure $SF_6$ accurately in the range 0-0.05% during wash-out. A typical concentration used in the inspired gas mixture for open-circuit wash-in when applying mass spectrometry for gas analysis is 4%. Thus, comparing inert gas rebreathing with e.g. 0.2% $SF_6$ as the initial concentration in the rebreathing bag and open-circuit multiple-breath wash-in using 4% $SF_6$ in the inspired gas mixture (i.e. a 20 times lower concentration) would result in >3,000 times less $SF_6$ consumed.

The fact that the open-circuit multiple-breath wash-in technique requires much more inert gas mixture than rebreathing makes the equipment more bulky and adds considerably to the overall cost of performing the procedure.

In the inert gas rebreathing method FRC is calculated by inert gas dilution alone according to the equation below:

$$FRC = V_{rb} \cdot \left( \frac{C_{rb,i}}{C_{eq,i}} - 1 \right) \quad (3)$$

in which
$V_{rb}$=Initial rebreathing bag volume
$C_{rb,i}$=Initial fractional concentration of insoluble gas in the rebreathing bag
$C_{eq,i}$=Equilibrium fractional concentration of insoluble gas obtained after mixing In the interest of brevity, dead spaces on each side of the valve are not accounted for, but these can easily be incorporated.

$V_{CE}$ is determined by integrating the part of the wash-out flow curve which has a sign corresponding to expiration (e.g. all positive flow signals) over time. By integrating flow (l/s) over time (s) a volume (l) is obtained.

All mathematical expressions and illustrations throughout this document are made using fractional concentrations of dry inert gas. Fractional concentrations can be replaced by partial pressures using appropriate conversion factors as known in the art.

Volumes can be expressed at different gas conditions using appropriate conversion factors as known in the art.

The gas dilution technique by inert gas rebreathing is more robust than the traditional wash-out technique for determination of FRC, because it is independent of the critical time alignment between gas analyser and flowmeter signals. Further, it relaxes the requirements to rise time of the gas analyser because only end-tidal concentrations are needed in determining the gas dilution, whereas in the open-circuit method a short rise time and accurate time alignment prior to integrating the product of flow and gas concentration signals are important in order to obtain accurate values of the flux of $SF_6$ in the rapid transitions during the beginning of expiration (phase II of the breath) and inspiration.

According to another aspect, the present invention also relates to a system adapted to determine the lung clearance index (LCI) of a test subject, said system comprising:
a rebreathing setup comprising at least a rebreathing bag prefilled with an inert tracer gas mixture for said test subject to rebreathe to and from during a rebreathing period;
at least one gas analyser for obtaining the fractional concentration of said inert tracer gas inhaled and exhaled by said test subject;
a flowmeter for monitoring the gas flow inhaled and exhaled by said test subject;
processing means for determining LCI of the lungs of a test subject using said obtained fractional concentration of said inert tracer gas from said rebreathing period to determine FRC and said gas flow to determine $V_{CE}$, required to clear said inert tracer gas concentration from the lungs below a predetermined fraction of the starting concentration, where LCI is determined as the ratio between $V_{CE}$ and FRC.

Hereby a system can be constructed that can achieve the same advantages as described above.

The gas analysers could be any apparatus suitable for obtaining the fractional concentration of the inert gas. Such apparatus could for instance be a mass spectrometer or an infrared photoacoustic multi-gas analyser, etc. In one embodiment of the invention the gas analysis is performed by a sensitive gas analyser with a high signal-to-noise ratio for example based on photoacoustic spectroscopy (PAS). The gas analysers can measure the end-tidal partial pressures or concentrations or a continuous partial pressure or concentration curve of the inert tracer gas.

The flowmeter could e.g. be a pneumotachometer, and is used to record the inspiratory and expiratory flows at the mouth. The pressure gradient measured is directly related to flow thus allowing a computer to derive a flow-curve measured in l/minute.

The processing means for determining LCI of the lungs of a test subject is comprised in the control system of the measuring system.

In one embodiment the system uses a gas mixture containing the inert tracer gas, SF6, which has very low solubility in blood and tissues and which is a good choice when using infrared gas analysis techniques.

In one embodiment the system uses an oxygen enriched gas mixture comprising the inert tracer gas to avoid oxygen deficiency during the rebreathing manoeuvre.

In one embodiment the system comprises a carbon dioxide ($CO_2$) scrubber. When the test subject rebreathes in a closed system, an accumulation of $CO_2$ will take place in the system. This build up of $CO_2$ can be experienced as uncomfortable by the test subject even though there is no lack of oxygen ($O_2$). This build up of $CO_2$ can be reduced by implementing a $CO_2$ scrubber in the flow way e.g. close to the rebreathing port right above the rebreathing bag or by implementing a small circuit using recirculation of gas through the $CO_2$ scrubber to avoid adding extra dead space.

In one embodiment the system comprises a small cylinder for containing the inert tracer gas mixture. Since the system has incorporated a sensitive gas analyser with a high signal-to-noise ratio and because rebreathing is the method of choice instead of open-circuit wash-in, a much smaller amount of inert gas is necessary for performing the test. The small cylinder contains approx. 150 ml of pressurized inert gas mixture which corresponds to 18 l of inert gas mixture at ambient pressure. In normal open-circuit wash-in the gas cylinder contains e.g. 1500 l of inert gas or more. The high concentration of inert gas inside the gas cylinder means that approx. only $1/10^{th}$ of the inhaled gas comes from the cylinder, the rest is atmospheric air or oxygen. The system can in one embodiment also comprise means to dilute the inert tracer gas mixture with air or oxygen. By using this dilution principle a much more compact system is obtained.

In one embodiment of the system, said processing means for determining LCI comprises processing means for determining FRC based on gas analysis alone and processing means for determining $V_{CE}$ required to clear the inert tracer gas concentration from the lungs below $1/40$th of the starting concentration. Hereby the same advantages as described above are achieved. The processing means is comprised in the control system of the measuring system.

In one embodiment of the system at least one gas analyser for obtaining the fractional concentration of said inert tracer gas inhaled and exhaled by said test subject under the inert gas rebreathing comprises means for obtaining the partial pressure of said inert tracer gas.

One embodiment of a system comprises:
a breathing assembly which can switch (manually or automatically) between an open circuit mode and a closed rebreathing mode (e.g. as illustrated in FIG. 3).
a gas dose facility enabling filling of the rebreathing bag to a known volume with a gas mixture containing the inert tracer gas. Alternatively, the rebreathing bag can be prepared manually.

Consider a test sequence where the test subject is performing first one rebreathing test followed by a wash-out period as the test sequence sketched in FIG. 5. The test periods do not have to be of equal length or of an equal number of breaths. The concentration of the Inert tracer gas is monitored and when the concentration is constant (below a predetermined threshold value regarding the fluctuation of the concentration), the first time period called wash-in, is over. Hereafter the wash-out period begins where the concentration of the inert tracer gas is monitored until the concentration has reached $1/40$ of the concentration in the beginning of the wash-out period. The wash-in period is used for accurate determination of the functional residual capacity (FRC) and the multiple-breath wash-out (MBW) is used for determination of the cumulative expired volume ($V_{CE}$) required to clear the inert tracer gas from the lungs.

According to another aspect, the present invention also relates to the use of the method according to the above to determine the lung clearance index (LCI) of a test subject.

According to another aspect, the present invention relates to a computer-readable medium having stored therein instructions for causing a processing unit to execute the above described method. Hereby the same advantages as described above are achieved.

BRIEF DESCRIPTION OF THE DRAWINGS

In the following, preferred embodiments of the invention will be described referring to the figures, where.

DESCRIPTION OF PREFERRED EMBODIMENTS

Figure 1:
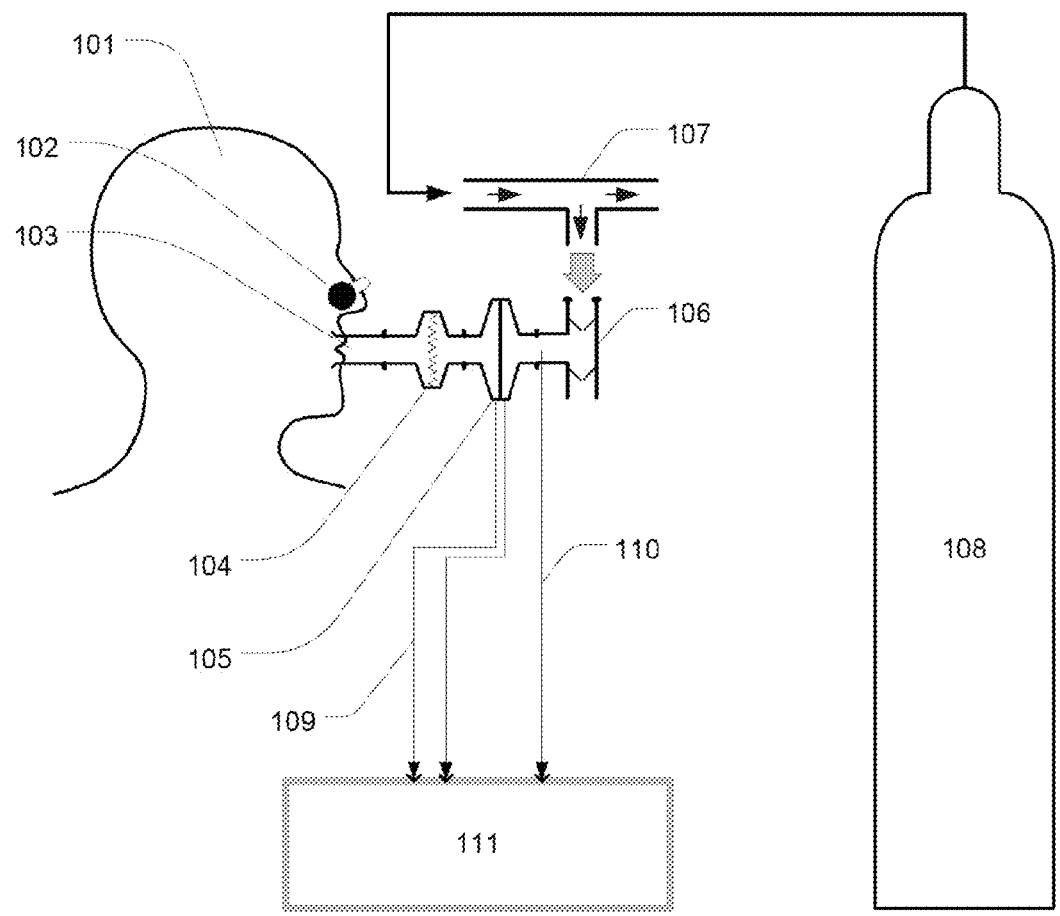
FIG. 1 (prior art) is a schematic diagram illustrating a conventional setup for multiple-breath inert gas wash-in/wash-out tests for determination of FRC and ventilation distribution (LCI) as known in the art.

FIG. 1 (prior art) is a schematic diagram illustrating a conventional setup for multiple-breath inert gas wash-in/wash-out tests for determination of FRC and ventilation distribution (LCI) as known in the art. The setup includes a bias flow of a mixture containing a non-resident inert tracer gas for wash-in in the flowpast assembly 107. A test subject 101 having the nose occluded with a nose clip 102 breathes through a mouthpiece 103, a bacterial filter 104, a respiratory flowmeter 105 and a non-rebreathing valve assembly 106. The gas reservoir 108 is coupled to a flowpast assembly 107 via a gas line. Flowmeter connection(s) 109 and a gas sample line 110 are also part of the setup.

To perform a multiple-breath inert gas wash-in/wash-out test, the test subject 101 inspires the non-resident inert tracer gas from the flowpast assembly 107 through the non-rebreathing valve assembly 106. The non-rebreathing valve assembly 106 is constructed by one-way valves allowing gas to flow in one direction only. Because of the construction of the valve 106, the test subject does not breathe the non-resident inert tracer gas back to the flowpast assembly 107 during exhalation. Instead the test subject expires to the surrounding air. The test subject 101 may use a face mask instead of nose clip 102 and mouthpiece 103. The analyser unit 111 consists of a measuring apparatus comprising flowmeter electronics and at least one gas analyser.

A typical test consists of a period where the test subject inspires from the flowpast and exhales to the surrounding air a number of times until the concentration of the tracer gas is constant e.g. below a predetermined threshold fluctuation (wash-in period) followed by a period where the test subject is breathing fresh air (wash-out period). During the testing (both during the wash-in and the wash-out period) the concentration in the inhaled and/or exhaled air of the inert gas in the mixture is measured by a fast responding gas analyser. Instead of gas concentration the gas analyser may equally well measure the partial pressure of the gas. The partial pressure can be obtained from the fractional concentration of dry gas or any other measure of gas concentration or pressure using appropriate conversion factors as known in the art. Also the flow of the inhaled and/or exhaled air is measured by means of the flowmeter 105. These measurements are made continuously.

Figure 2:
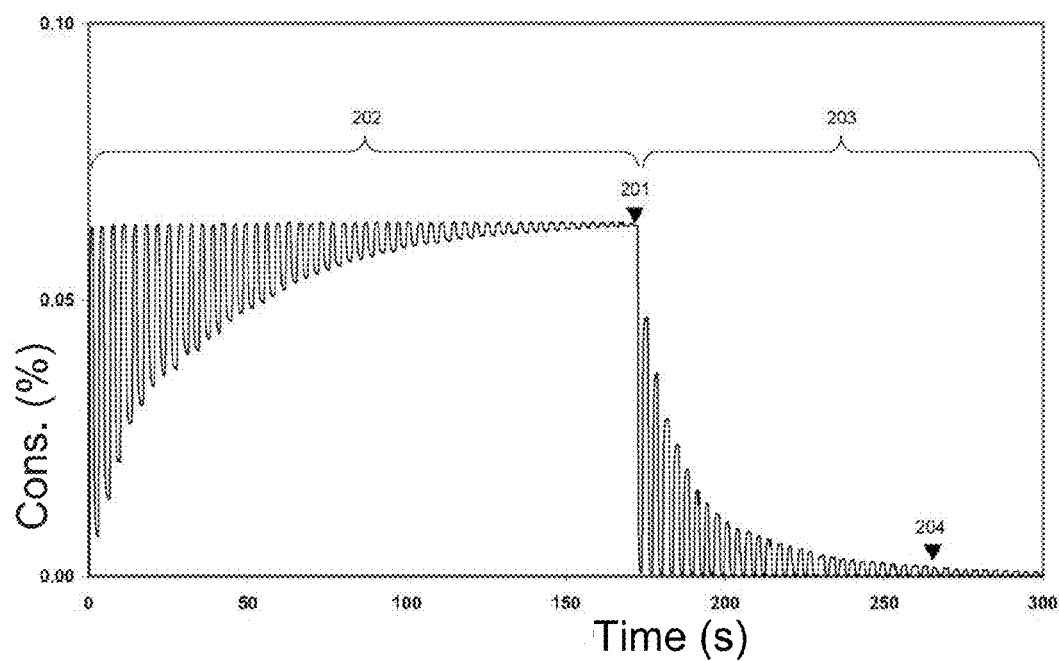
FIG. 2 (prior art) illustrates a curve from a conventional multibreath wash-in/wash-out.

FIG. 2 (prior art) outlines a curve from a conventional multibreath wash-in/wash-out test from where LCI can be determined. The insoluble gas, $SF_6$, has become the gas of choice for measurement of LCI. The concentration of $SF_6$ is monitored and when the concentration is constant (below a predetermined threshold fluctuation) 201, the first time period called wash-in 202 is over. Hereafter the wash-out period 203 begins where the concentration of $SF_6$ is monitored until the concentration has reached 1/40 of the concentration in the beginning of the wash-out period 204. The cumulative expired volume ($V_{CE}$) required to clear the lungs of the gas down to 1/40 of its start concentration can then be used in combination with the functional residual capacity (FRC) to determine the LCI of the test subject. In the conventional MBW test the FRC is calculated from the net volume of inert gas exhaled divided by the difference in end-tidal concentration at the start and end of the wash-out:

$$FRC = \frac{\text{Net volume of inert gas exhaled}}{C_{ET,start} - C_{ET,end}} \quad (2)$$

As the net volume of inert gas exhaled (numerator) is obtained by integration of the product of respiratory flow and tracer gas concentration (i.e. expired and re-inspired tracer gas volumes on a breath-by-breath basis), accurate determination of the FRC requires a rapid dynamic response and data acquisition rate of the gas analyser. Proper alignment in time of the respiratory flow signal and tracer gas concentration prior to the calculation is also critical. This makes demands on the performance of the gas analyser and the calibration of the equipment.

Figure 3:
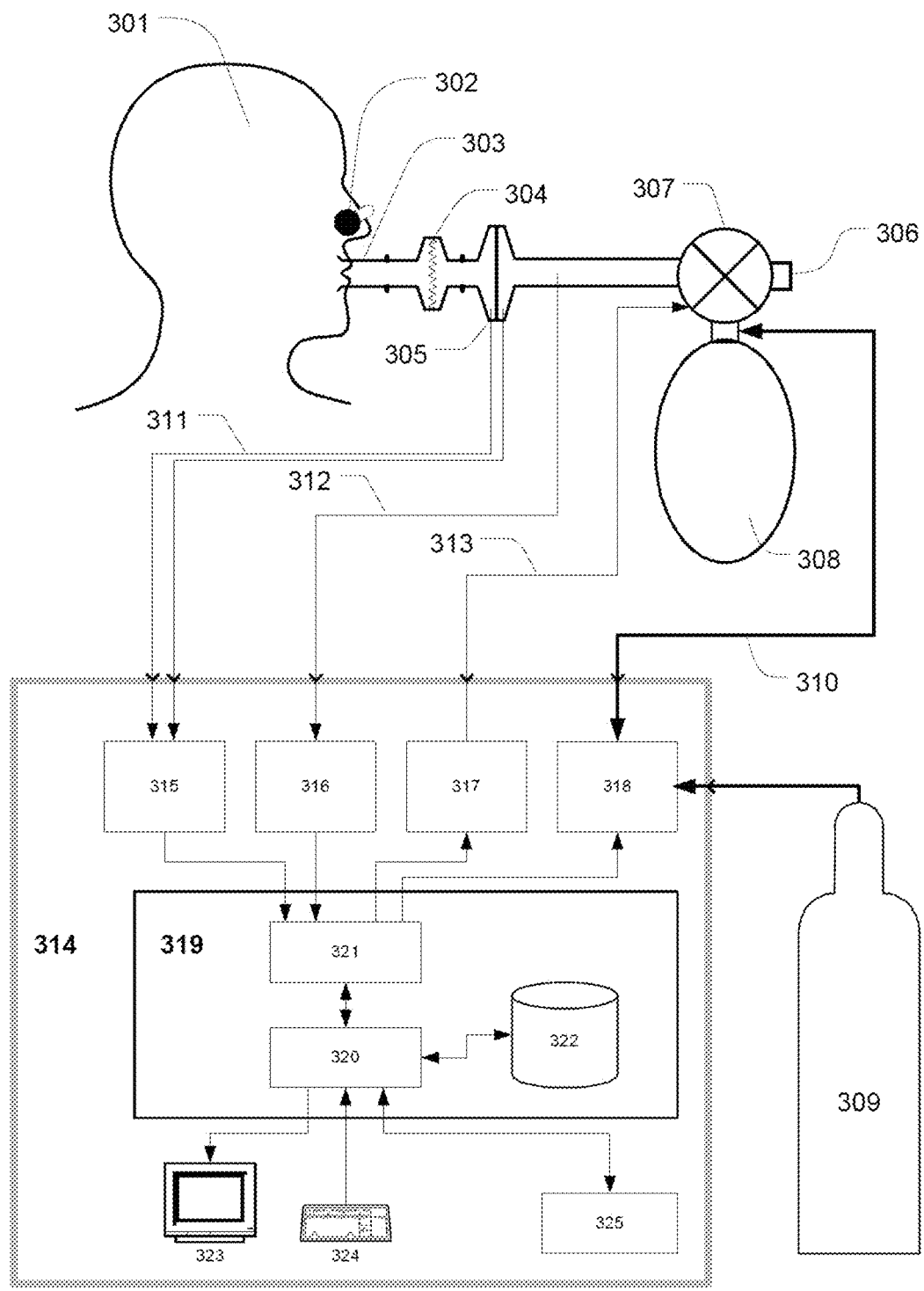
FIG. 3 is a schematic diagram illustrating a setup for wash-in/wash-out tests using inert gas rebreathing for determination of FRC and ventilation distribution (LCI) as used in conjunction with the disclosed invention.

FIG. 3 is a schematic diagram illustrating a setup for wash-in/wash-out tests using inert gas rebreathing for determination of FRC and ventilation distribution (LCI) as used in conjunction with the disclosed invention. A test subject 301 having the nose occluded with a nose clip 302 breathes through a mouthpiece 303, a bacterial filter 304, a respiratory flowmeter 305 and one port 306 of a rebreathing valve assembly 307. A rebreathing bag 308 is connected to the valve assembly and evacuated and pre-filled with a gas mixture from a gas reservoir 309 via a gas line 310. Flowmeter connection(s) 311 and a gas sample line 312 are also part of the setup.

To perform a rebreathing test the valve assembly 307 is switched (e.g. automatically by controlling line 313) to allow the test subject 301 to inspire and rebreathe to and from the bag 308 for a certain amount of time until the valve assembly 307 is switched back again. The test subject 301 may use a face mask instead of nose clip 302 and mouthpiece 303. The control system 314 of the measuring apparatus consists of flowmeter electronics 315, at least one gas analyser 316, a valve control unit 317 (unless the valve assembly is manually driven) and a gas control unit 318 (unless the bag is prepared manually). A control unit 319 is also included, comprising a computing/processing unit (CPU) 320 with control interfaces 321, one or more program and data storage devices 322 and user interfaces for example comprising a display 323 and a keyboard, touch screen or similar input device 324. A data input/output module 325 may also be included.

The processing unit (CPU) can e.g. comprise processing means for determining LCI of the lungs of a test subject using the obtained fractional concentration of the inert tracer gas measured by the gas analysers and the gas flow measured by the flowmeter and associated flowmeter electronics. Also, the processing unit can e.g. comprise processing means for determining FRC based on gas analysis alone and processing means for determining $V_{CE}$ required to clear the inert tracer gas concentration from the lungs below 1/40th of the starting concentration.

Prior to the rebreathing tests the rebreathing bag is filled with a known volume of an inert gas mixture. During the testing the test subject is breathing through the respiration valve, which allows switching from breathing air to rebreathing the inert gas mixture from the bag and switching back again.

A typical test consists of a period where the test subject is breathing to and from the bag (rebreathing period) followed by a period where the test subject is breathing fresh air (wash-out period). During the testing (both during the rebreathing and the wash-out period) the concentration in the inhaled and/or exhaled air of the inert gas in the mixture is measured by a fast responding gas analyser 316. Instead of gas concentration the gas analyser may equally well measure the partial pressure of the gas. The partial pressure can be obtained from the fractional concentration of dry gas or any other measure of gas concentration or pressure using appropriate conversion factors as known in the art. Also the flow of the inhaled and/or exhaled air is measured by means of the flowmeter 315. These measurements are made continuously.

Figure 4:
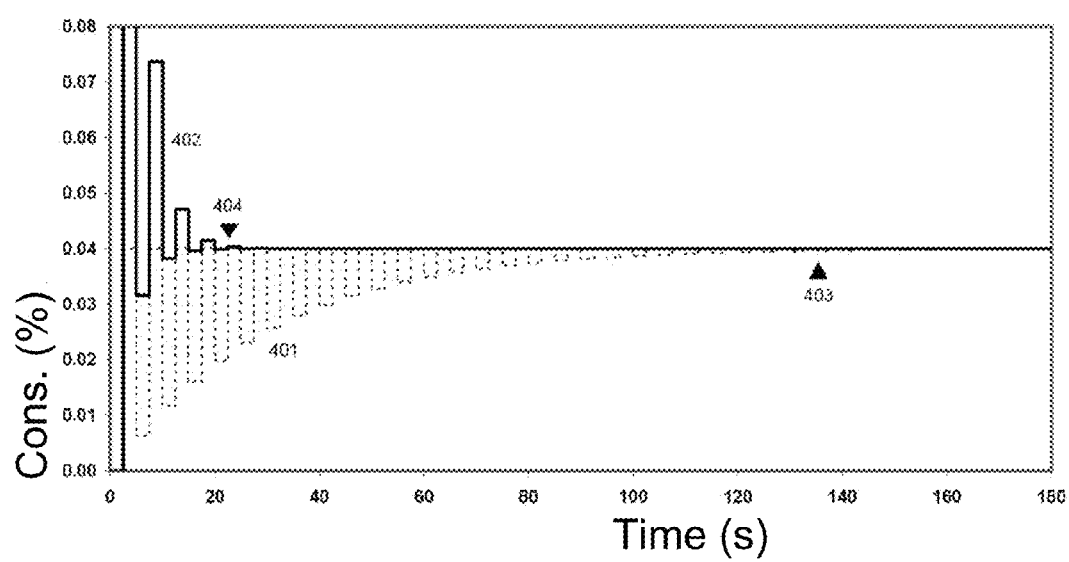
FIG. 4 is an example comparing the wash-in of an inert tracer gas by inert gas rebreathing as used in conjunction with the disclosed invention (solid curve) and by conventional wash-in as known in the art (dashed curve), respectively. The simulation in the example is performed using the following input values: FRC=3.0 l, dead space $V_D$=0.2 l, bag volume $V_{RB}$=tidal volume $V_T$=0.8 l. Ratio between wash-in breaths $n_{MBW}/n_{RB}$=6.

FIG. 4 is an example comparing the wash-in curve of an inert tracer gas by conventional multibreath wash-in 401 (dotted line) with the wash-in curve of an inert tracer gas by rebreathing wash-in 402 (solid line) as used in conjunction with the disclosed invention, respectively. The simulation is based on the single compartment lung model and the example is performed using the following input values: FRC=3.0 l, deadspace $V_D$=0.2 l, and bag volume $V_{RB}$=tidal volume $V_T$=0.8 l. It can be seen that the rebreathing wash-in method 402 reaches equilibration 404 much faster, 5-10 times (ratio between wash-in breaths $n_{MBW}/n_{RB}$=6 in this example), than the conventional multibreath wash-in 401, 403, and since the conventional open-circuit wash-in phase lasts longer than the subsequent wash-out phase this means a reduction of total test time by typically more than 50%.

Figure 5:
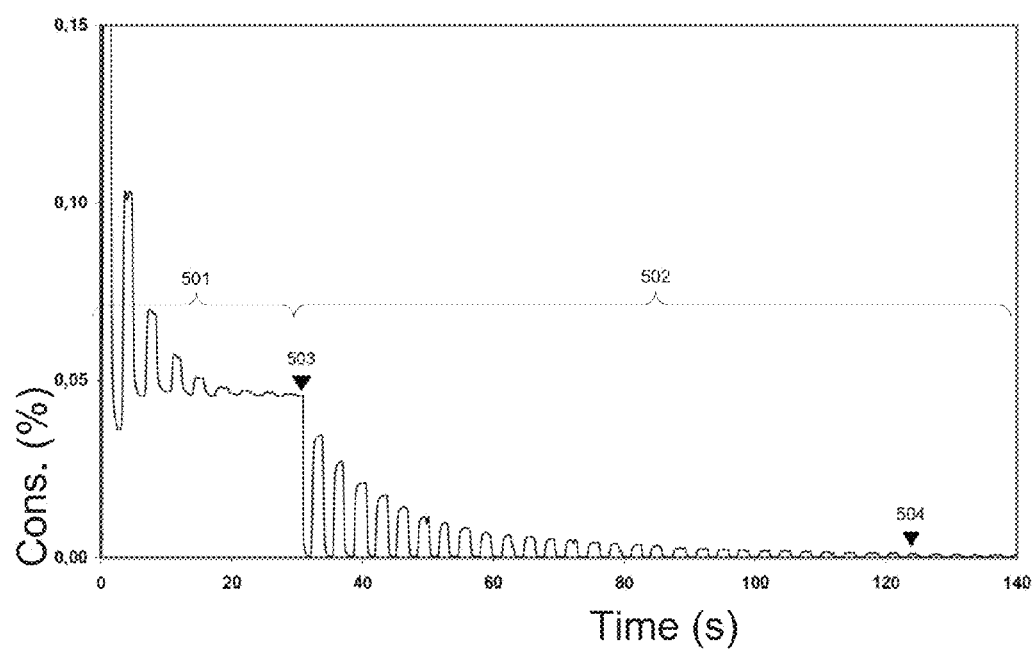
FIG. 5 is an example of a test sequence as used in conjunction with the disclosed invention comprising an inert gas rebreathing manoeuvre and a subsequent wash-out period.

FIG. 5 is a typical example of a test sequence as used in conjunction with one embodiment of the disclosed invention comprising two pulmonary gas exchange techniques for determination of LCI. LCI represents the number of lung volume turnovers (i.e. FRCs) that the subject must breathe to clear the lungs from the tracer gas (by convention, to an end-tidal concentration of 1/40th of the starting concentration over three subsequent breaths). Disregarding the correction for external dead space the equation is:

$$LCI = \frac{V_{CE}}{FRC} \quad (1)$$

Inert gas rebreathing manoeuvre 501 is used for rapid wash-in of the inert tracer gas followed by a subsequent multiple-breath wash-out period 502. The concentration of the inert tracer gas is monitored and when the concentration is constant 503 (below a predetermined threshold value regarding the fluctuation of the concentration), the first time period called wash-in 501, is over. Hereafter the wash-out period 502 begins where the concentration of the inert tracer gas is monitored until the concentration has reached 1/40 of the concentration in the beginning of the wash-out period 504.

The wash-in period is used for accurate determination of the functional residual capacity (FRC) which is calculated by inert gas dilution alone according to the equation below:

$$FRC = V_{rb} \cdot \left( \frac{C_{rb,i}}{C_{eq,i}} - 1 \right) \quad (3)$$

in which
$V_{rb}$=Initial rebreathing bag volume
$C_{rb,i}$=Initial fractional concentration of insoluble gas in the rebreathing bag
$C_{eq,i}$=Equilibrium fractional concentration of insoluble gas obtained after mixing In the interest of brevity dead spaces on each side of the valve are not accounted for, but these can easily be incorporated.

The multiple-breath wash-out (MBW) is used for determination of the cumulative expired volume ($V_{CE}$) required to clear the inert tracer gas from the lungs. $V_{CE}$ is determined by integrating the part of the wash-out flow curve which has a sign corresponding to expiration (e.g. all positive flow signals) over time. By integrating flow (l/s) over time (s), a volume (l) is obtained.

The gas dilution technique by inert gas rebreathing is more robust than the traditional wash-out technique for determination of FRC, because it is independent of the critical time alignment between gas analyser and flowmeter signals. Further, it relaxes the requirements to rise time of the gas analyser because only end-tidal concentrations are needed in determining the gas dilution, whereas in the open-circuit method a short rise time and accurate time alignment prior to integrating the product of flow and gas concentration signals are important in order to obtain accurate values of the flux of $SF_6$ in the rapid transitions during the beginning of expiration (phase II of the breath) and inspiration.

It should be noted that the above-mentioned means of implementation illustrate rather than limit the invention, and that those skilled in the art will be able to suggest many alternative means of implementation without departing from the scope of the appended claims. Rather, the words used in the specification are <words of description rather than limitation, and it is understood that various changes may be made without departing from the scope of the invention. The word 'comprising' does not exclude the presence of other elements or steps than those listed in a claim. The invention can be implemented by means of hardware and software comprising several distinct elements, and by means of a suitably programmed computer. In a device claim enumerating several means, several of these means can be implemented by one and the same item of hardware or software. The mere fact that certain measures are recited in mutually different dependent claims does not indicate that a combination of these measures cannot be used to advantage.

The invention claimed is:

1. A method of determining a lung clearance index (LCI) of a test subject, said method comprising the steps of:
   in a closed rebreathing assembly, rebreathing an inert tracer gas mixture having a starting concentration of an inert tracer gas until a constant concentration of the inert tracer gas is reached to wash-in the inert tracer gas, wherein the closed rebreathing assembly comprises a rebreathing bag filled with a volume of the inert tracer gas mixture corresponding to resting tidal volume of the test subject;
   performing multiple-breath wash-out until end-tidal tracer gas concentration has fallen below a predetermined fraction of the starting concentration; and
   determining the lung clearance index (LCI) by:
      determining functional residual capacity (FRC) by gas analysis alone from the inert gas rebreathing;
      determining, via a processor, cumulative expired volume ($V_{CE}$) required to clear the inert tracer gas concentration from the lungs below the predetermined fraction of the starting concentration; and calculating, via the processor, the LCI as a ratio between $V_{CE}$ and FRC.

2. The method according to claim 1, wherein the inert tracer gas is $SF_6$.

3. The method according to claim 1, wherein the inert tracer gas mixture is an oxygen enriched gas mixture.

4. The method according to claim 1, wherein the gas analysis is performed by a photoacoustic spectroscopy (PAS) sensitive gas analyzer.

5. A system adapted to determine a lung clearance index (LCI) of the lungs of a test subject, said system comprising:
    a closed rebreathing setup configured to allow a test subject to rebreathe an inert tracer gas mixture having a starting concentration of an inert tracer gas until a constant concentration of the inert tracer gas is reached to wash-in the inert tracer gas during a rebreathing period, wherein the closed rebreathing setup comprises at least a rebreathing bag prefilled with a volume of the inert tracer gas mixture corresponding to resting tidal volume of said test subject to rebreathe to and from during the rebreathing period;
    at least one gas analyzer for obtaining fractional concentration of said inert tracer gas inhaled and exhaled by said test subject;
    a flowmeter for monitoring gas flow inhaled and exhaled by said test subject;
    processing means for determining the LCI of the lungs of the test subject using said obtained fractional concentration of said inert tracer gas from said rebreathing period to determine functional residual capacity (FRC) and said gas flow to determine cumulative expired volume ($V_{CE}$) required to clear said inert tracer gas concentration from the lungs below a predetermined fraction of the starting concentration, wherein LCI is determined as a ratio between $V_{CE}$ and FRC.

6. The system according to claim 5, wherein the inert tracer gas is $SF_6$.

7. The system according to claim 5, wherein the inert tracer gas mixture is an oxygen enriched gas mixture.

8. The system according to claim 5, wherein the at least one gas analyzer comprises a photoacoustic spectroscopy (PAS) sensitive gas analyzer.

9. The system according to claim 5, wherein the closed rebreathing setup further comprises a $CO_2$ scrubber.

10. The system according to claim 5, wherein the closed rebreathing setup further comprises a cylinder for containing a pressurized inert tracer gas mixture.

11. The system according to claim 5, wherein the processing means for determining LCI of the lungs of the test subject comprises processing means for determining the FRC based on gas analysis alone and processing means for determining the $V_{CE}$ required to clear the inert tracer gas concentration from the lungs below 1/40th of the starting concentration.

12. The system according to claim 5, wherein the at least one gas analyzer for obtaining the fractional concentration of said inert tracer gas inhaled and exhaled by said test subject comprises means for obtaining the partial pressure of said inert tracer gas.

13. The system according to claim 5, wherein the closed rebreathing setup further comprises a respiration valve assembly which allows switching from breathing air to rebreathing the inert tracer gas mixture.

14. The system according to claim 13, wherein the respiration valve assembly is controlled manually.

15. A non-transitory computer readable medium having stored therein instructions for causing a processing unit of a system switchable between an open circuit configuration and a closed rebreathing configuration to execute the determining of a lung clearance index (LCI) of a test subject through the following steps:
    initiating the flow of an inert tracer gas at a starting concentration in the closed rebreathing configuration for rebreathing wash-in of the inert tracer gas by the test subject until a constant concentration of the inert tracer gas is reached;
    determining when an end-tidal concentration of the inert tracer gas has fallen below a predetermined fraction of the starting concentration during multiple-breath wash-out in the open circuit configuration; and
    determining the lung clearance index (LCI) by:
        determining, via the processing unit, functional residual capacity (FRC) by gas analysis alone from the inert gas rebreathing;
        determining, via the processing unit, cumulative expired volume ($V_{CE}$) required to clear the inert tracer gas concentration from the lungs below the predetermined fraction of the starting concentration; and
        calculating, via the processing unit, the LCI as a ratio between $V_{CE}$ and FRC.

16. The non-transitory computer readable medium according to claim 15, wherein the steps for determining LCI further comprise: controlling, via the processing unit, a respiration valve.

* * * * *